United States Patent [19]

Hiltebrandt

[11] 4,392,485
[45] Jul. 12, 1983

[54] ENDOSCOPE

[75] Inventor: Siegfried Hiltebrandt, Knittlingen, Fed. Rep. of Germany

[73] Assignee: Richard Wolf GmbH, Knittlingen, Fed. Rep. of Germany

[21] Appl. No.: 256,029

[22] Filed: Apr. 21, 1981

[30] Foreign Application Priority Data

Feb. 17, 1981 [DE] Fed. Rep. of Germany ... 8104329[U]

[51] Int. Cl.³ .............................................. A61B 1/06
[52] U.S. Cl. ..................................................... 128/6
[58] Field of Search ...................... 128/4, 5, 6, 7, 8, 9, 128/10, 11

[56] References Cited

U.S. PATENT DOCUMENTS

| | | | |
|---|---|---|---|
| 3,261,351 | 7/1966 | Wallace | 128/6 |
| 3,941,121 | 3/1976 | Olinger et al. | 128/6 |
| 3,945,375 | 3/1976 | Banko | 128/6 |
| 4,086,919 | 5/1978 | Bullard | 128/6 |
| 4,217,891 | 8/1980 | Carson | 128/6 |
| 4,261,346 | 4/1981 | Wettermann | 128/6 |
| 4,294,234 | 10/1981 | Matsuo | 128/6 |

OTHER PUBLICATIONS

World Medical News–Sep. 31, 1972, "Laparoscopy-Sterilization".

*Primary Examiner*—Kyle L. Howell
*Assistant Examiner*—Max F. Hindenburg
*Attorney, Agent, or Firm*—Kinzer, Plyer, Dorn & McEachran

[57] ABSTRACT

The invention relates to endoscopes specially laparoscopes of known art with an external shaft through which passes a channel for guiding instruments and a fibre light conductor and an optic.

According the invention the channel of the shaft is increased in its inner diameter and the diameter of the optic is decreased in such a manner that now not only usual instruments being present in a practice but also instruments can pass the channel which have an increased diameter for instance the fixing of clips or elastic rings onto a Fallopian tube.

2 Claims, 5 Drawing Figures

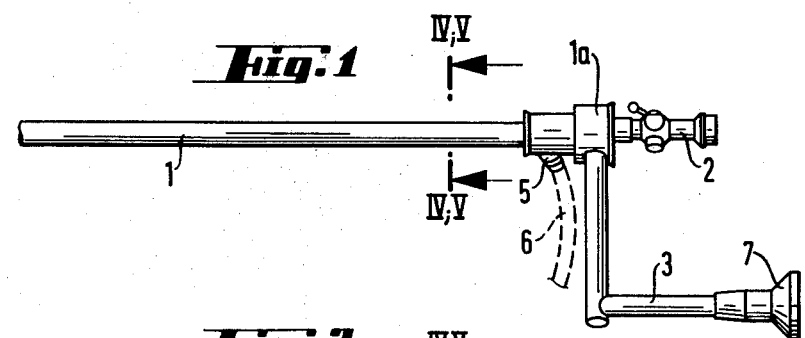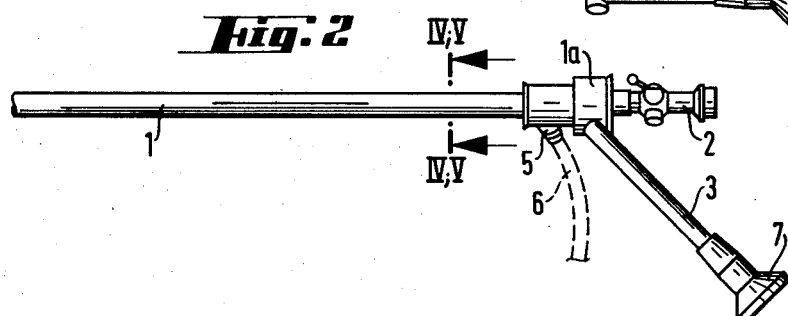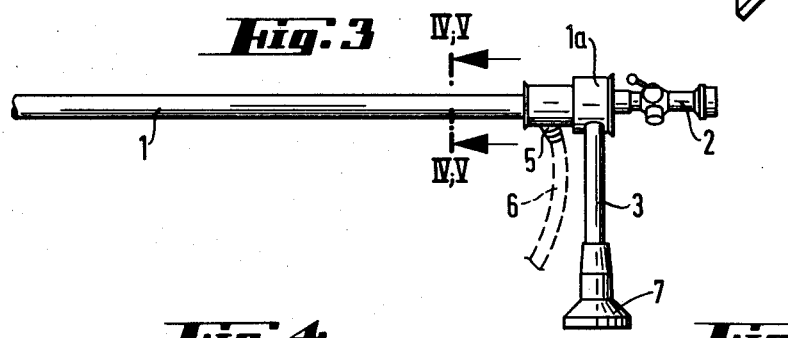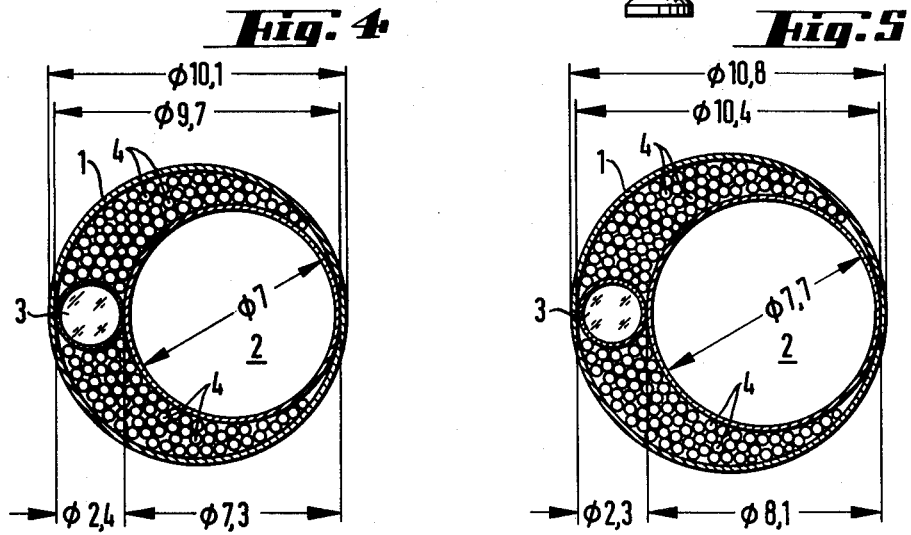

ENDOSCOPE

BACKGROUND OF THE INVENTION

The invention relates to endoscopes specially laparoscopes having an external shaft through which passes a channel for guiding medical instruments and a fibre light conductor and an optic. The proximal part of said optic is one or several times bent away from the enlarged proximal part of the shaft. The inner diameter of the said known shaft is at least 9.7 mm and maximal 10.4 mm.

The external shaft of the above said laparoscopes has an external diameter of 10 mm up to 10.8 mm, so that the laparotomy can be small enough for avoiding damage to blood vessels or nerves or the like. Such damage can be present if the external diameter of the shaft should be increased, because then the laparotomies will be too long. The known shafts with the described measurements have a longitudinal running channel for the medical instruments, the inner diameter of which is 3.0 to 5.0 mm and the diameter of the optic is about 4.0 to 5.0 mm. All instruments as probes, biobsy forceps, other forceps, coagulation probes or the like are accommodated to the shafts of said known measurements. But by using shafts with the known channel the surgeon could not guide a medical instrument through the channel which will be used for fixing clips or elastic rings to the Fallopian tube. Therefore because of the increased diameter of such instruments it was necessary to use a different laparoscope with an increased diameter of the shaft, but it required a longer laparotomy again.

The object of the invention consists in that the usual known diameter of the shaft of laparoscopes may be maintained so that besides all instruments used till now other instruments of an increased diameter for instance instruments for fixing clips or elastic rings onto the Fallopian tube can be guided through the channel or passage of the laparoscope.

SUMMARY OF THE INVENTION

Therefore the invention consists in that by using laparoscope shafts identified in the introduction the diameter of the optic running through the shaft is about 20 to 25%, and the inner diameter of the channel for guiding through the instruments is about 75 to 80% of the inner diameter of the shaft.

The increasing of the channel for the instruments with highly decreased diameter of the optic are sufficient in respect to all instruments being in dispute and having different diameters and which will be used for operations and treatments in the abdomen cavity. Therefore the surgeon now is in the position to maintain all his actual instruments and also instruments with an increased diameter. For the surgeon it is no more necessary to use laparoscopes with different diameters of the shaft.

BRIEF DESCRIPTION OF THE DRAWINGS

The present invention will now be described in relation to the drawings which show in FIGS. 1-3: the schematic side views of usual shafts of a laparoscope FIGS. 4-5: two enlarged sections along line II—II of FIGS. 1-3 with different diameters of the optic and of the channel of the instruments.

DETAILED DESCRIPTION OF A PREFERRED EMBODIMENT

Laparoscopes which generally will be introduced into the abdomen through a trocar guide consist of a shaft 1; through the length of it passes a channel 2 for instruments, an optic 3 and a fibre light conductor 4. The fibre light conductor 4 fills the room above and/or under the channel 2 and the optic 3. This fibre light conductor is collected in a proximal collecting pipe 5, which will be connected to a light source by a light transmitting fibre bundle (dotted line 6). The optic at the proximal widened end 1a of the shaft 1 is extends from the ocular 7 with a single or two folded angle (FIGS. 3 and 1) or is inclined to the shaft 1 as shown in FIG. 2.

For achieving the object of the invention the inner diameter of channel 2 has been increased up to 70% of the inner diameter of the shaft (FIG. 4), that means up to about 7 mm, and in relation to FIG. 5 the inner diameter of channel 2 is increased up to 75% of the inner diameter of the shaft, that means up to about 77 mm. Correspondingly the diameter of the optic is decreased to about 25% that means to 2.4 mm or in the other case to about 20% or about 2.3 mm. Therefore now with one and the same shaft all present operating instruments and also instruments of an increased diameter, for instance to fix a clip or elastic ring, can pass through the channel 3 of the laparoscope.

I claim:

1. Endoscope having an external shaft through which passes a guide channel for receiving instruments, a fibre light conductor and an optic, the proximal part of said optic being turned away from one side of the proximal part of the shaft, and in which the inner diameter of the shaft is at least 9.7 mm but maximal 10.4 mm, wherein the guide channel for receiving instruments of one kind for the treatment of the abdomen and also separate instruments of another kind for fixing clips or elastic rings onto an internal organ is characterized with a diameter of 70-75% of the shaft diameter for receiving both kinds of instruments, and a second channel for receiving an optic having a diameter of 20-25% of the shaft diameter so that together the instrument channel and optic channel occupy about 95% of the internal diameter of said shaft.

2. An endoscope according to claim 1 which is a laparoscope.

* * * * *